(12) United States Patent
Gillespie, Jr. et al.

(10) Patent No.: US 6,778,914 B1
(45) Date of Patent: Aug. 17, 2004

(54) DYNAMIC INTERPHASE-LOADING APPARATUS AND METHOD OF USING THE SAME

(75) Inventors: John W. Gillespie, Jr., Hockessin, DE (US); Metin Tanoglu, Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 09/528,379

(22) Filed: Mar. 17, 2000

(51) Int. Cl.[7] .............................................. G06F 19/00
(52) U.S. Cl. ........................................ 702/34; 73/763
(58) Field of Search ............................. 702/34, 33–36, 702/41–44, 66, 108, 113–114, 158, 183; 73/760, 763, 781, 788–789, 791, 794; 428/375, 378, 408

(56) References Cited

U.S. PATENT DOCUMENTS

| | | | | |
|---|---|---|---|---|
| 4,373,039 A | * | 2/1983 | Mueller et al. ............. 523/205 |
| 4,662,228 A | * | 5/1987 | Tse ............................ 73/842 |
| 4,842,933 A | | 6/1989 | Cizmecioglu ............... 428/378 |
| 4,979,992 A | * | 12/1990 | Bache ........................ 106/644 |
| 5,195,046 A | * | 3/1993 | Gerardi et al. ............... 702/35 |
| 5,269,181 A | * | 12/1993 | Gibson et al. ............... 73/160 |
| 5,288,555 A | * | 2/1994 | Monette et al. ............. 428/375 |
| 5,817,944 A | * | 10/1998 | Chung ........................ 73/768 |
| 5,984,448 A | * | 11/1999 | Yanagawa .................... 347/10 |
| 6,023,980 A | * | 2/2000 | Owen et al. .................. 73/797 |

\* cited by examiner

*Primary Examiner*—Marc S. Hoff
*Assistant Examiner*—Mary Catherine Baran
(74) *Attorney, Agent, or Firm*—Connolly Bove Lodge & Hutz LLP

(57) ABSTRACT

The present invention comprises a dynamic interphase-loading apparatus and method for testing the interfacial shear strength, stress-strain response, energy absorbing capability and durability of an interphase region of a fiber/matrix composite under quasi-static to high strain rates. The apparatus provides a load to the fiber/matrix interphase under high loading rates. The apparatus includes means for continuously monitoring the load applied to the fiber/matrix composite and providing a signal representative thereof, and means for monitoring the displacement of the interphase and providing a signal representative thereof. The apparatus further includes a computer that receives the load signal and the displacement signal, and generates chemical properties of the interphase of the fiber/matrix composite.

15 Claims, 7 Drawing Sheets

DISPLACEMENT RESPONSE OF PIEZOELECTRIC ACTUATOR

DYNAMIC INTERPHASE-LOADING APPARATUS AND METHOD OF USING THE SAME

The present invention has Government rights assigned to the Army Research Laboratory under contract number DAAL01-96-2-0048.

BACKGROUND OF THE INVENTION

A. Field of the Invention

The present invention relates generally to an apparatus for testing composite materials, and, more particularly to a dynamic interphase-loading apparatus for testing composite materials and a method of using the same.

B. Description of the Related Art

Recent studies of composite materials show that the properties of the resin at the fiber/matrix interface region are different than those of the bulk resin. The fiber/matrix region forms during processing of the resin and is known as the interphase. Fiber/matrix interphase properties play an important role on the performance of the composite. Modification of the interphase could change the modes of failure and energy-absorption characteristics. Therefore, significant efforts have been directed at developing a fundamental understanding of the role of interphase. In order to properly understand interphase, one must first be able to accurately test the mechanical properties of the interphase.

Several macromechanical testing techniques have been developed to test the ballistic and impact properties of the composites under dynamic loading conditions (i.e., under high strain rates), as well as quasi-static loading conditions. As shown in FIG. 1(a), such dynamic macromechanical testing techniques include the Hopkinson bar, gas gun, plate impact, and weight drop techniques. As shown in FIG. 1(b), macromechanical test techniques, such as short beam shear and flexural bending, have been used to characterize interphase under quasi-static conditions. However, these techniques fail to directly obtain interphase-related data or to isolate the effects of interphase because mechanical loading applied to the composite induces complex stress states within the fiber/matrix interphase that are not well defined. Thus, these techniques provide useful but qualitative information about interphase.

Micromechanical testing techniques that can directly characterize the interphase properties have been developed, but are limited to testing interphase properties under quasi-static loading conditions. As shown in FIG. 1(c), such micromechanical techniques include the single fiber fragmentation, fiber pull-out, and microindentation techniques.

Thus, there is a need for a new micromechanical test technique that can directly characterize the interphase properties under dynamic (high-strain rate) loading conditions.

SUMMARY OF THE INVENTION

An object of the invention is to provide a micromechanical testing technique that obtains interphase-related data under quasi-static and dynamic (high-strain rate and fatigue) loading conditions.

Another object of the invention is to provide an apparatus that permits directly testing of the interfacial shear strength, energy absorbing capability, shear stress ($\tau$)-shear strain ($\delta$) behavior and elastic modulus and durability (fatigue life, residual strength after fatigue loading or exposure to a hot, wet environment) of various-sized fiber/matrix systems under quasi-static and dynamic (high strain rate) loading conditions.

A still further object of the invention is provide a testing apparatus and method that overcomes the problems associated with the related art.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a dynamic interphase-loading apparatus (DILA) for testing the mechanical properties of an interphase region of a fiber/matrix composite under quasi-static to dynamic loading conditions, the apparatus comprising: means for providing a quasi-static to dynamic load to the fiber/matrix interphase; means for continuously monitoring the load applied to the fiber/matrix composite and providing a signal representative thereof; means for continuously monitoring the displacement of the interphase of the fiber/matrix composite and providing a signal representative thereof; means for forming various inputs signal to activate the piezoelectric actuator and to generate various displacement rates; and a computing means for receiving the load signal from the load monitoring means, for receiving the displacement signal from the displacement monitoring means, and for providing an input signal to the piezoelectric actuator, the computing means having a memory means connected to a processing means, wherein the processing means stores the load signal in the memory means, generates the input signal supplied to the piezoelectric actuator, and generates information representing the mechanical properties of the interphase of the fiber/matrix composite.

To further achieve the objects, the present invention comprises a method for testing the mechanical properties of an interphase region of a fiber/matrix composite under quasi-static to dynamic loading conditions, the method comprising the steps of: using a diamond tip as a probe to load the interphase; providing a quasi-static to dynamic load to the fiber/matrix interphase; debonding the fiber from the matrix at the interphase region and eventually pushing the fiber out from matrix; continuously monitoring the load applied to the fiber/matrix composite and providing a signal representative thereof; continuously monitoring the displacement of the interphase of the fiber/matrix composite and providing a signal representative thereof; receiving the load signal and the displacement signals in a computing means having a memory means connected to a processing means; providing a control signal to the piezoelectric actuator, via the computing means; and using the processing means of the computing means to store the load signal in the memory means, generate the control signal supplied to the piezoelectric actuator, and generate information representing the mechanical properties of the interphase of the fiber/matrix composite.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention. In the drawings:

FIG. 1 (d) is a block diagram showing a test method used to characterize the mechanical properties of the interphase, in accordance with a preferred embodiment of the present invention;

DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts.

The present invention is drawn broadly to a dynamic interphase-loading apparatus (DILA) that measures interphase properties under dynamic (high-strain rate and fatigue) as well as quasistatic loading conditions. The apparatus uses a method based upon the debonding of a fiber from a matrix at the interphase region. The method permits determination of, for example, the interfacial shear strength, shear stress-strain response, and energy absorbing capability of various sized fiber/matrix interphase systems under quasi-static and high-strain-rate loading conditions. Additionally, the method allows characterizing the durability of the fiber/matrix interphase. Medium or high frequency fatigue behavior (fatigue life and residual strength after fatigue loading) or hygrothermal durability of the interphase can also be qualified using the DILA.

Figures 1A, 1B, 1C, 1D:
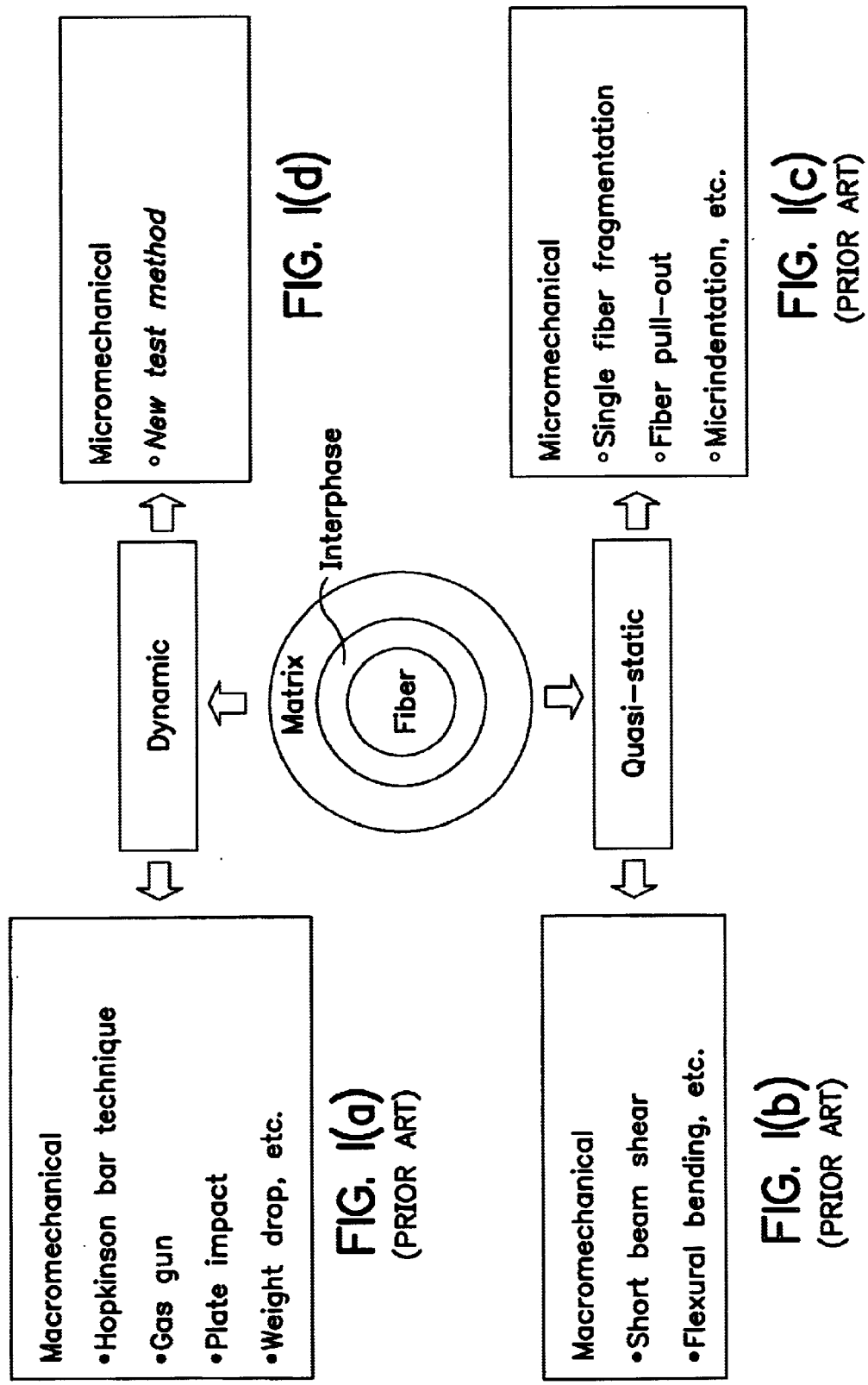
FIGS. 1(a) through 1(c) are block diagrams showing conventional test methods used to characterize the mechanical properties of the interphase.
Figure 2:
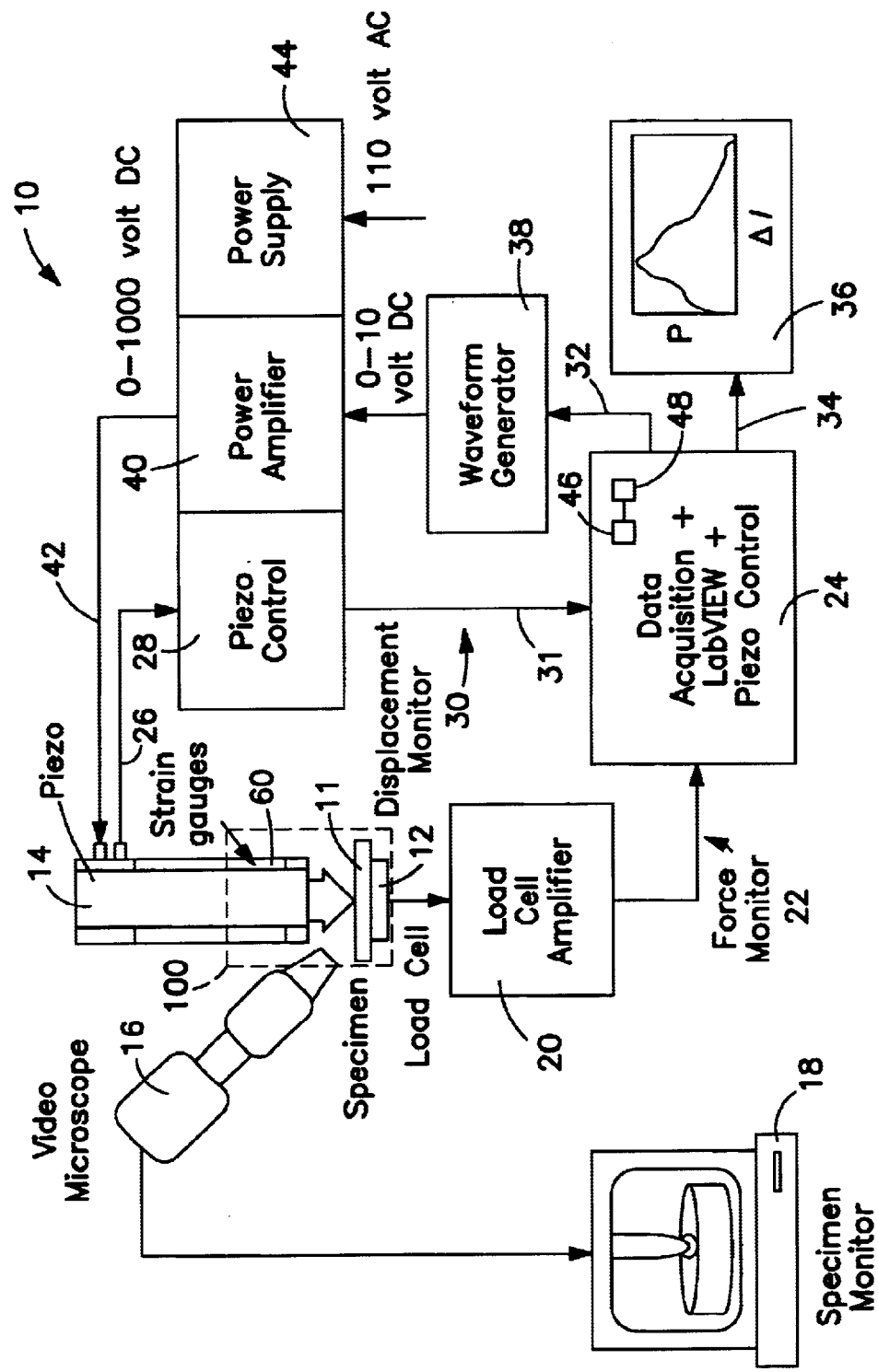
FIG. 2 is a block diagram of a dynamic interphase-loading apparatus (DILA) in accordance with the preferred embodiment of the present invention.

More specifically, as shown in FIG. 2, the present invention comprises a dynamic interphaseloading apparatus 10 for testing the mechanical properties of an interphase region of a fiber/matrix composite 11. Apparatus 10 generally comprises a piezoelectric (PZT) displacement actuator 14 for providing a load to fiber/matrix composite 11 under quasi-static and dynamic (high strain rates and fatigue) loading conditions. Apparatus 10 further comprises a piezo load cell 12 connected to an amplifier 20 for monitoring the load applied to fiber/matrix interphase 11 and providing a signal 22 representative thereof. Piezoelectric actuator 14 includes a strain gauge bridge 60 for monitoring the displacement of the interphase of fiber/matrix composite 11 and providing a signal 26 representative thereof. Strain gauge signal 26 connects to a piezo monitor device 28. The piezo monitor device 28 is a voltage supply that conditions the strain gauge signal 26 and then provides a signal 31 representative of displacement. Finally, apparatus 10 comprises a computing means 24 for receiving load signal 22 from load cell 12, for receiving displacement signal 31 from piezo monitor device 28, and for providing a control signal to piezoelectric actuator 14. Computing means 24 has a memory means 46 connected to a processing means 48. Processing means 48 stores load signal 22 and displacement signal 31 in memory means 46, generates the control signal supplied to piezoelectric actuator 14, and generates information representing the mechanical properties of the interphase of the fiber/matrix composite 11. Computing means 24 sends the mechanical properties information to a display means 36 for display and analysis.

As embodied herein, fiber/matrix composite 11 is preferably analyzed with a video microscope 16. Video microscope 16 provides a signal representing the image of fiber/matrix composite 11 to a specimen monitor 18. Specimen monitor 18 visually displays the microscopic image of fiber/matrix composite 11 for a user of apparatus 10.

Computing means 24 preferably comprises a typical microprocessor-based computing device such as an IBM-compatible personal computer. Computing means 24 further comprises a processing means 46 such as a conventional microprocessor, and a memory means 48 such as a conventional computer-readable memory capable of being encoded with software programs. The software program preferably used with the present invention is LabVIEW manufactured by National Instruments™ Corporation of Austin, Tex. LabVIEW is a graphical programming development environment based on the G programming language for data acquisition and control, data analysis, and data presentation.

Figure 7:
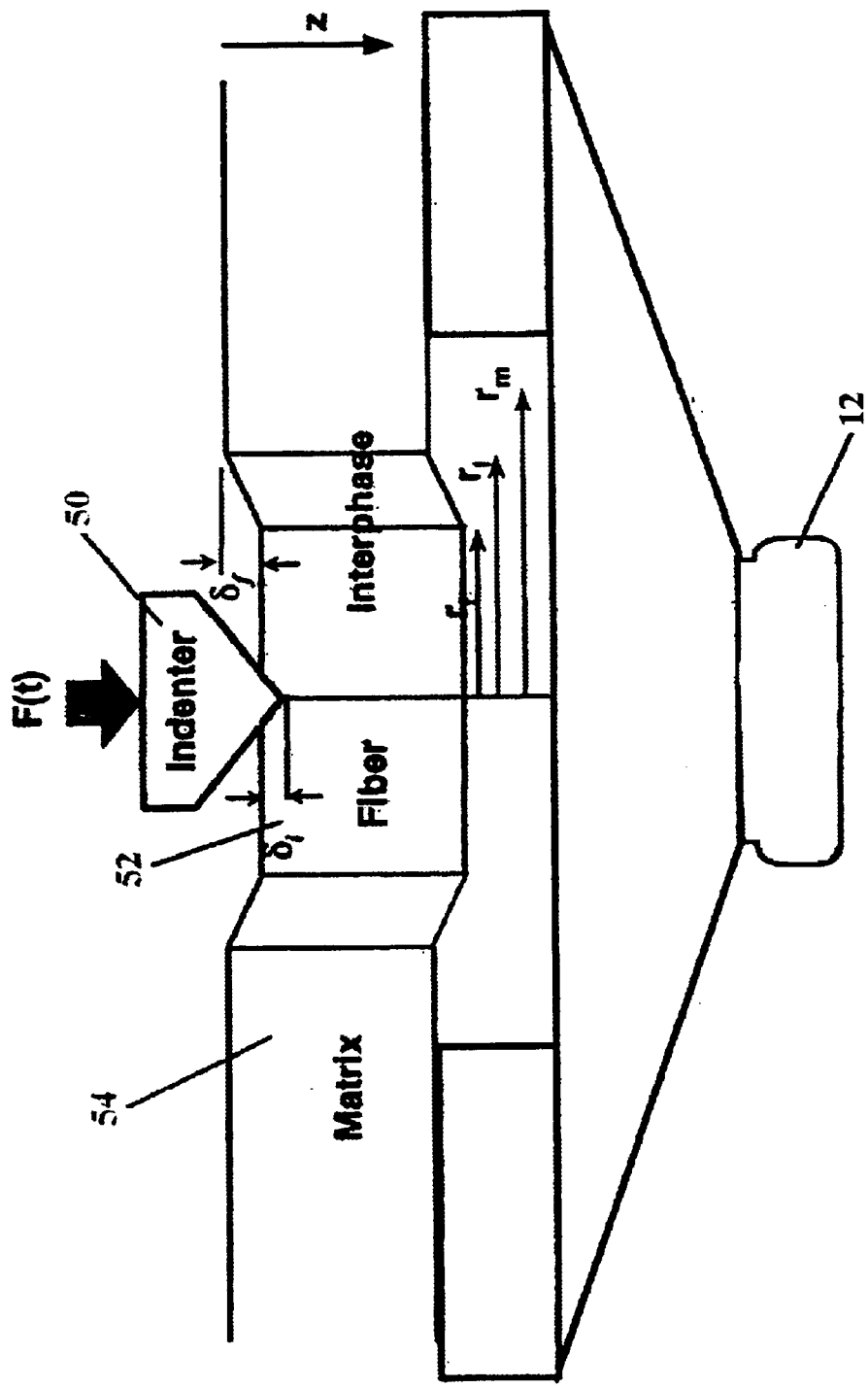
FIG. 7 is an exploded view showing the test configuration and a micro-debonding process of an interphase of a fiber/matrix composite using the dynamic interphase-loading apparatus of FIG. 2.

Since piezoelectric components generate large forces within a short response time, this fast expansion capability of piezoelectric actuator 14 is used to load the interphase region of fiber/matrix composite 11 under high strain-rate conditions. The response of piezoelectric actuator 14 is related to the form of the given input signal to piezoelectric actuator 14 and also the power output of a piezo-driven power amplifier 40. The present invention also makes use of a high-power amplifier 40 (typically having at least a 500-watt peak output power) in conjunction with piezoelectric actuator 14. High-power amplifier 40 enables piezoelectric stack assembly 14 to generate a high rate of displacement, typically in the range of quasi-static to $4500\mu$/sec displacement rates, and to exert forces up to one ton. FIG. 7 shows the displacement response of the piezo as a function of time. Experiments are repeatable even for high displacement rates, since the response of piezoelectric actuator 14 preferably does not change from test to test.

To vary the rate of interphase loading, the form of the input is changed. The desired input signal is generated using a stored in memory means 46 and the generated signal 32 is stored in memory of waveform generator 38. The stored signal 32 is used as an input signal to drive piezoelectric actuator 14 via power amplifier 40. During a test, a diamond tip 50 (as shown in FIG. 7), attached to piezoelectric stack assembly 14, is positioned at the center of selected fiber 52 using an x-y-z positioning system, video microscope 16, and specimen monitor 18. Once the contact is made between the diamond tip 50 and fiber 52, the system is triggered using the triggering function of waveform generator 38 to send input to piezoelectric actuator 14. Piezoelectric stack assembly 14 provides a load F to the interphase of fiber/matrix composite 11. As shown in FIG. 7, load F causes a fiber 52 to detach from a matrix 54 of fiber/matrix composite 11, and to eventually be pushed out from matrix 54. Displacement of diamond tip 50 and change in load F is continuously monitored during the test using high frequency data acquisition system 24.

Figure 3:
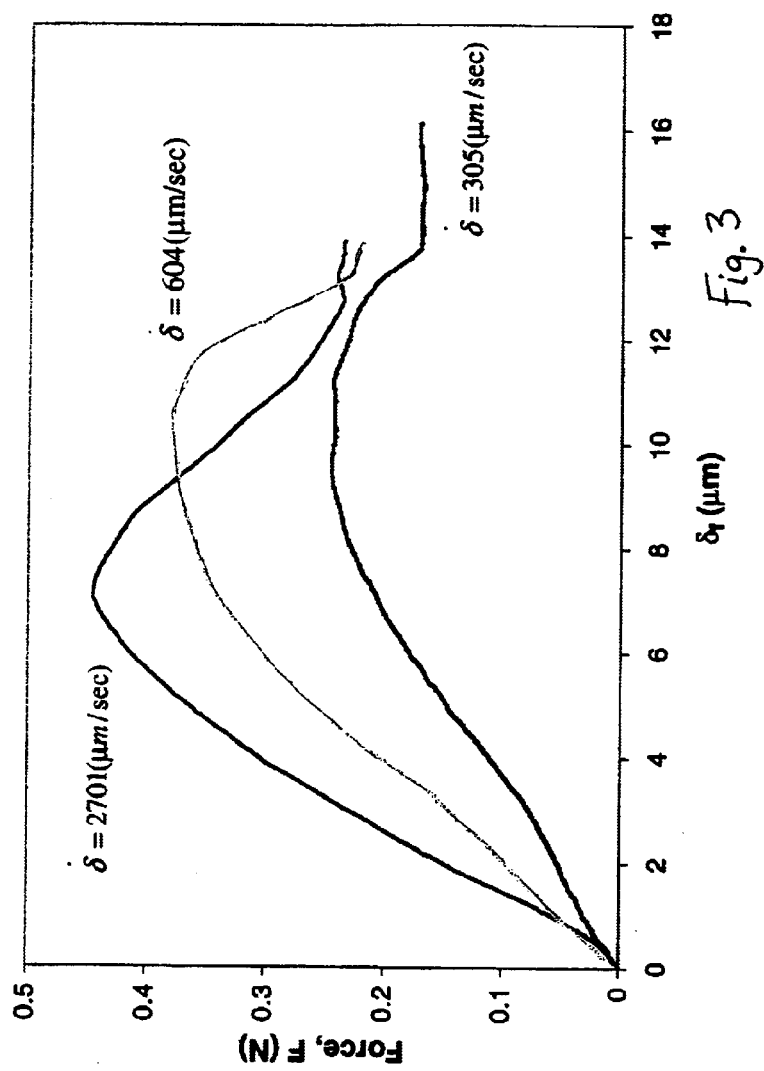
FIG. 3 is a graph showing the force versus the displacement of the fiber/matrix interphase obtained using the dynamic interphase-loading apparatus of FIG. 2.
Figure 4:
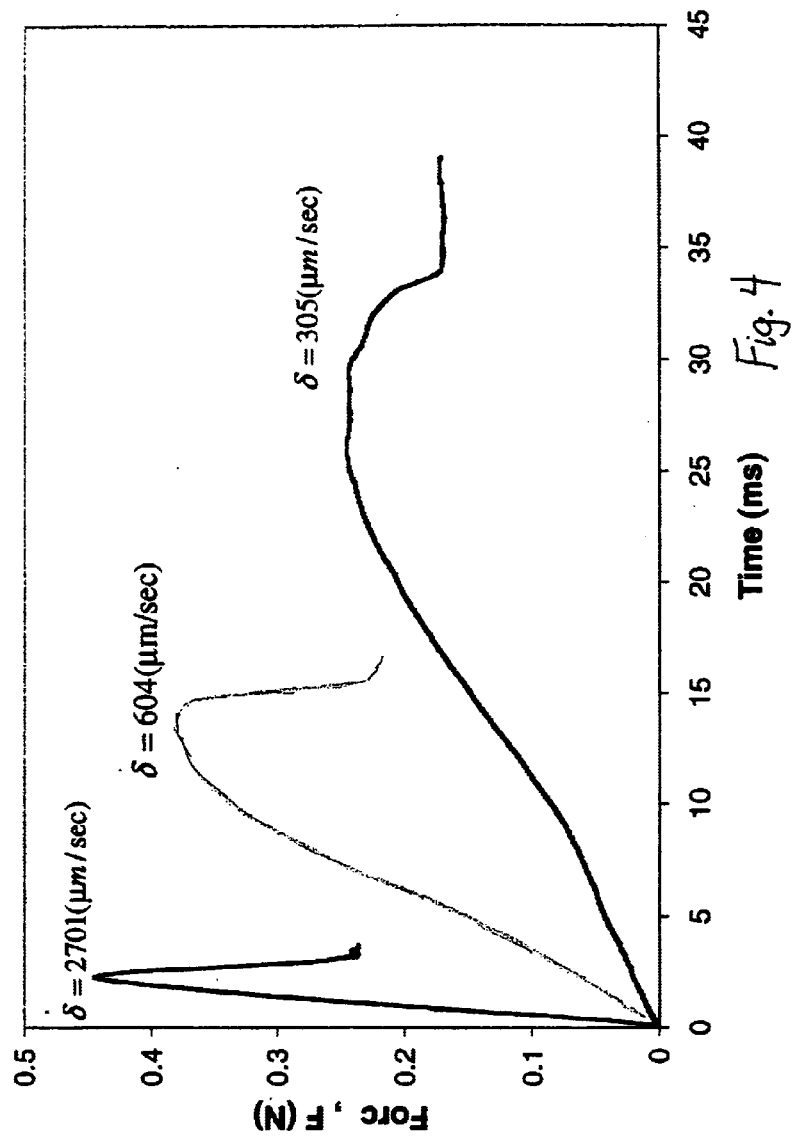
FIG. 4 is a graph showing the signal generated (force versus time) by a load cell amplifier of the dynamic interphase-loading apparatus of FIG. 2.
Figure 5:
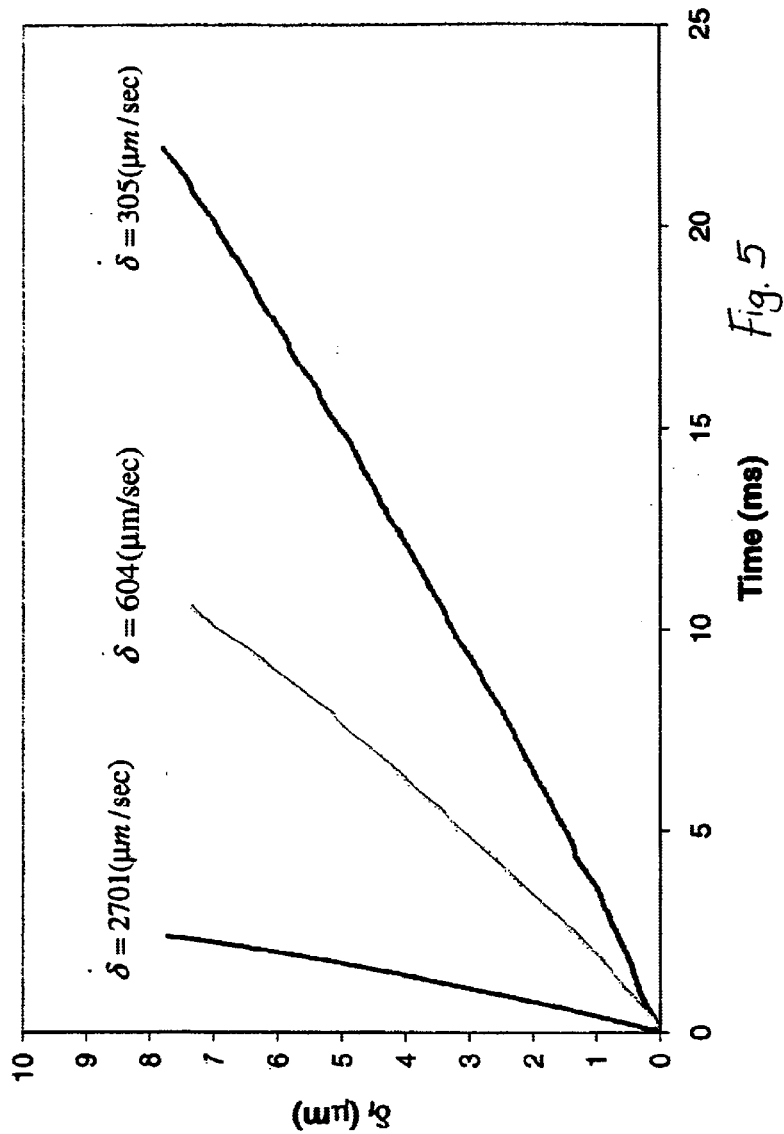
FIG. 5 is a graph showing the signal generated (displacement versus time) by a piezoelectric actuator of the dynamic interphase-loading apparatus of FIG. 2.
Figure 6:
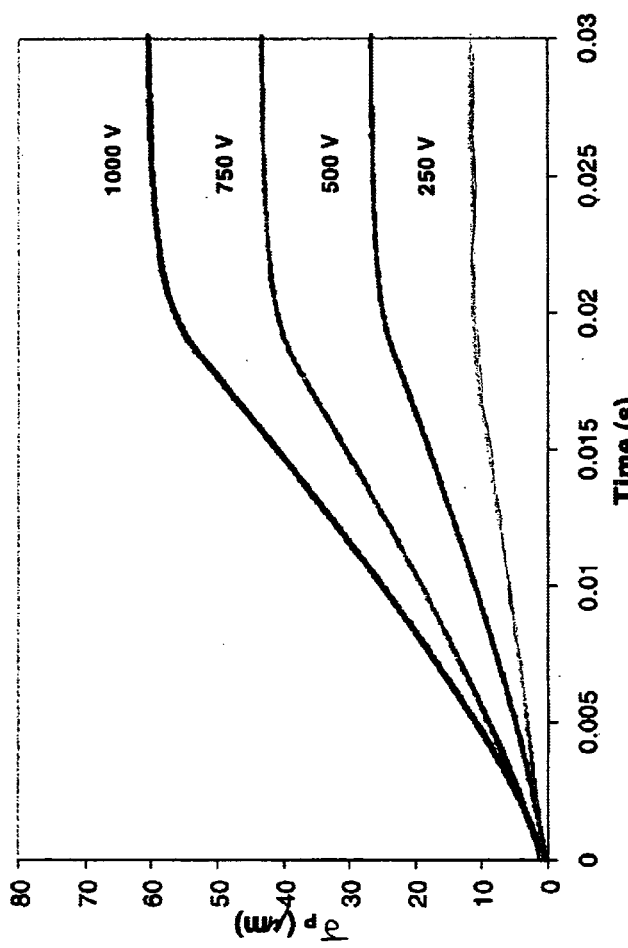
FIG. 6 is a graph showing the response signal generated (displacement versus time) by the piezoelectric stack assemblies of the dynamic interphase-loading apparatus of FIG. 2.

FIG. 3 is a graph showing the load versus the displacement of the interphase using dynamic interphase-loading apparatus (DILA) 10. FIG. 4 is a graph showing the signal generated displacement versus time) by piezo monitor 28 of the dynamic interphase-loading apparatus. FIG. 5 is a graph showing the signal generated (load versus time) by load cell amplifier 20 of the dynamic interphase-loading apparatus. FIG. 6 is a graph showing the signal generated (displacement versus time) by strain gauge bridge 60 of the dynamic interphase-loading apparatus.

It will be apparent to those skilled in the art that various modifications and variations can be made in the dynamic interphase-loading apparatus of the present invention and in construction of this apparatus without departing from the scope or spirit of the invention. As an example, the dynamic interphase-loading apparatus may be used to measure the micro- and nano-mechanical properties of thin-film coatings at different loading rates. Also, an environment control can be used with the DILA apparatus to determine the durability of the interphase properties or the effects of the service conditions on it. For this purpose, a hot stage and humidity chamber 100 can be included with the DILA to expose the interphase to hydrothermal (hot and wet) conditions.

Other embodiments of the invention will be apparent to those skilled in the art from consideration and practice of the invention disclosed herein. It is intended that the specification and examples be considered as exemplary only, with a true scope and spirit of the invention being indicated by the following claims.

What is claimed is:

1. A dynamic interphase-loading apparatus (DILA) for testing the mechanical properties of an interphase region of a fiber/matrix composite under dynamic loading conditions, the apparatus comprising:

means for providing a to dynamic load to the fiber/matrix interphase;

means for continuously monitoring the load applied to the fiber/matrix composite and providing a signal representative thereof;

means for continuously monitoring the displacement of the interphase of the fiber/matrix composite and providing a signal representative thereof;

means for forming various input signals to activate the load providing means and to generate various displacement rates; and a computing means for receiving the load signal from the load monitoring means, for receiving the displacement signal from the displacement monitoring means, and for providing an input signal to the load providing means, the computing means having a memory means connected to a processing means, wherein the processing means stores the load signal in the memory means, generates the input signal supplied to the load providing means, and generates information representing the mechanical properties of the interphase of the fiber/matrix composite.

2. The dynamic interphase-loading apparatus as recited in claim 1, wherein the information representing the mechanical properties generated by the computing means comprises the interfacial shear strength, frictional sliding stress, energy absorbing capability, and stress-strain response of the interphase of the fiber/matrix composite.

3. The dynamic interphase-loading apparatus as recited in claim 1, wherein the computing means generates information representing the durability of the interphase of the fiber/matrix composite.

4. The dynamic interphase-loading apparatus as recited in claim 3, wherein the information representing the durability of the interphase of the fiber/matrix composite comprises the fatigue life and the residual strength after fatigue loading or exposure to a hygrothermal environment of the interphase of the fiber/matrix composite.

5. The dynamic interphase-loading apparatus as recited in claim 1, wherein the load providing means comprises a piezoelectric actuator.

6. The dynamic interphase-loading apparatus as recited in claim 1, wherein the displacement monitoring means comprises a strain gauge bridge.

7. The dynamic interphase-loading apparatus as recited in claim 1, wherein the load monitoring means comprises a load cell.

8. The dynamic interphase-loading apparatus as recited in claim 1, wherein the means for forming various input signals comprises a waveform generator.

9. A method for testing the mechanical properties of an interphase region of a fiber/matrix composite under dynamic loading conditions, the method comprising the steps of:

using a diamond tip as a probe to load the interphase;

providing a dynamic load with a load mechanism to the fiber/matrix interphase;

debonding the fiber from the matrix at the interphase region and eventually pushing the fiber out from the matrix;

continuously monitoring the load applied to the fiber/matrix composite and providing a signal representative thereof;

continuously monitoring the displacement of the interphase of the fiber/matrix composite and providing a signal representative thereof;

receiving the load signal and the displacement signals in a computing means having a memory means connected to a processing means;

providing a control signal to the load mechanism, via the computing means; and using the processing means of the computing means to store the load signal in the memory means, generate the control signal supplied to the load mechanism, and generate information representing the mechanical properties of the interphase of the fiber/matrix composite.

10. The method for testing the mechanical properties of an interphase region of a fiber/matrix composite as recited in claim 9, wherein the information representing the mechanical properties generated by the computing means comprises the interfacial shear strength, frictional sliding stress, energy absorbing capability, and stress-strain response of the interphase of the fiber/matrix composite.

11. The method for testing the mechanical properties of an interphase region of a fiber/matrix composite as recited in claim 9, further comprising the step of using the processing means of the computing means to generate information representing the durability of the interphase of the fiber/matrix composite.

12. The method for testing the mechanical properties of an interphase region of a fiber/matrix composite as recited in claim 11, wherein the information representing the durability of the interphase of the fiber/matrix composite comprises the fatigue life and the residual strength after fatigue loading or exposure to a hygrothermal environment of the interphase of the fiber/matrix composite.

13. The method for testing the mechanical properties of an interphase region of a fiber/matrix composite as recited in claim 9, wherein the load mechanism comprises a piezoelectric actuator.

14. The method for testing the mechanical properties of an interphase region of a fiber/matrix composite as recited in claim 9, wherein the displacement of the interphase is monitored with a strain gauge bridge.

15. The method for testing the mechanical properties of an interphase region of a fiber/matrix composite as recited in claim 9, wherein the load applied to the interphase is monitored with a load cell.

* * * * *

UNITED STATES PATENT AND TRADEMARK OFFICE
CERTIFICATE OF CORRECTION

PATENT NO.  : 6,778,914 B1
DATED       : August 17, 2004
INVENTOR(S) : John W. Gillespie, Jr. et al.

It is certified that error appears in the above-identified patent and that said Letters Patent is hereby corrected as shown below:

Title page,
Item [57], ABSTRACT,
Line 10, after "interphase" insert -- of the fiber/maxtrix interphase --.
Line 13, after "generates" delete "chemical" and insert -- information representing the mechanical --.

Column 5,
Line 24, after "providing a" delete "to".

Signed and Sealed this

Twenty-fifth Day of January, 2005

JON W. DUDAS
*Director of the United States Patent and Trademark Office*